United States Patent [19]

Franks

[11] Patent Number: 4,858,621

[45] Date of Patent: Aug. 22, 1989

[54] FOOT PRESSURE MEASUREMENT SYSTEM

[75] Inventor: Christopher I. Franks, Hatharage, England

[73] Assignee: Biokinetics, Inc., Bethesda, Md.

[21] Appl. No.: 168,953

[22] Filed: Mar. 16, 1988

[51] Int. Cl.[4] .............................................. A61B 5/10
[52] U.S. Cl. ...................................... 128/779; 33/512
[58] Field of Search ...................... 128/779, 774, 782; 73/705; 33/512; 356/445

[56] References Cited

U.S. PATENT DOCUMENTS 4,691,709  9/1987  Cohen .................................. 128/667

OTHER PUBLICATIONS

"Dynamic Pedobarograph Reference Manual".
R. P. Betts et al., "Critical Light Reflection at a Plastic/Glass Interface and Its Application to Foot Pressure Measurements," 4 *Journal of Medical Engineering & Technology* 136, May 1980.
R. P. Betts et al., "A Device for Measuring Planter Pressures Under the Sole of the Foot," 7 *Engineering in Medicine* 223 (1978).
C. I. Franks et al., "Microprocessor-based Image Processing System for Dynamic Foot Pressure Studies," *Medical and Biological Engineering & Computing*, pp. 566-572, Sep. 1983.
R. P. Betts, "Static and Dynamic Foot Pressure Measurements in Clinical Orthopaedics," *Medical and Biological Engineering & Computing* 674 (Sep. 1980).
R. P. Betts, "Static and Dynamic Foot Pressure Measurements in the Management of the Insensitive Foot," *Proceedings of the International Conference on Biomedics and Clinical Kinealogy of Head and Foot*, I. I. T., Madras, India 101 (Dec. 16-18, 1985).
R. P. Betts et al., "A Simple Grey-Scale to Colour Converter," 3 *Journal of Medical Engineering and Technology* 31 (Jan. 1979).
M. Lord, "Foot Pressure Measurement: A Review of Methodology," 3 Journal of Biomedical Engineering 91 (Apr. 1981).

Primary Examiner—Max Hindenburg
Assistant Examiner—John C. Hanley
Attorney, Agent, or Firm—Lowe, Price, LeBlanc Becker & Shur

[57] ABSTRACT

An improved foot pressure measurement system wherein pressure measurements are obtained from the variation of light output from an illuminated glass or transparent plate. A reflective material on the top surface of the plate causes an increase in light intensity escaping from the plate when pressure is applied to the reflective material. The accuracy and resolution of the pressure measurements are improved by obtaining a reference measurement of the background light intensity and distribution before pressure is applied and subsequently subtracting this background light from the light patterns produced when pressure is applied. The reflectance characteristics of the system are improved by using a photographic paper as the reflective material.

14 Claims, 12 Drawing Sheets

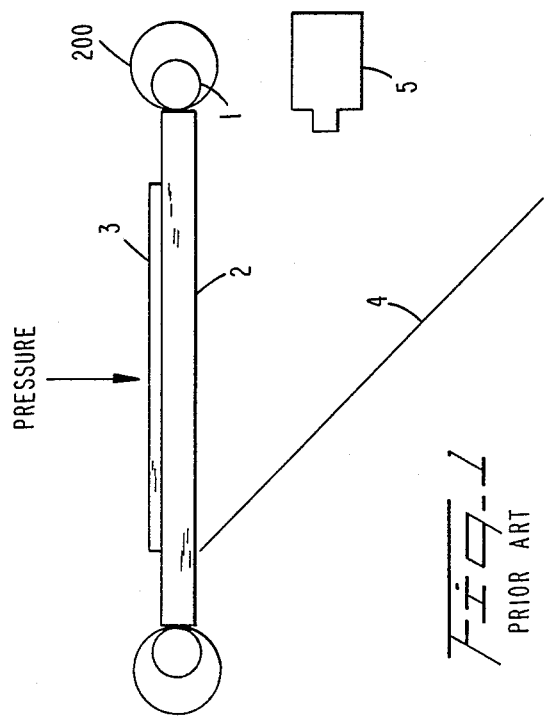
Fig. 1 PRIOR ART
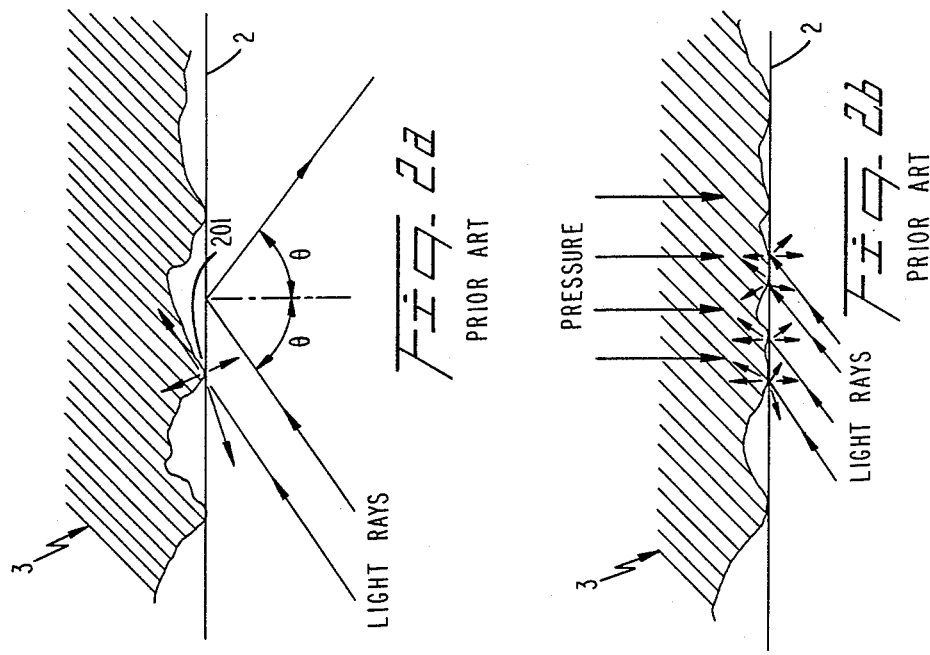
Fig. 2a PRIOR ART
Fig. 2b PRIOR ART

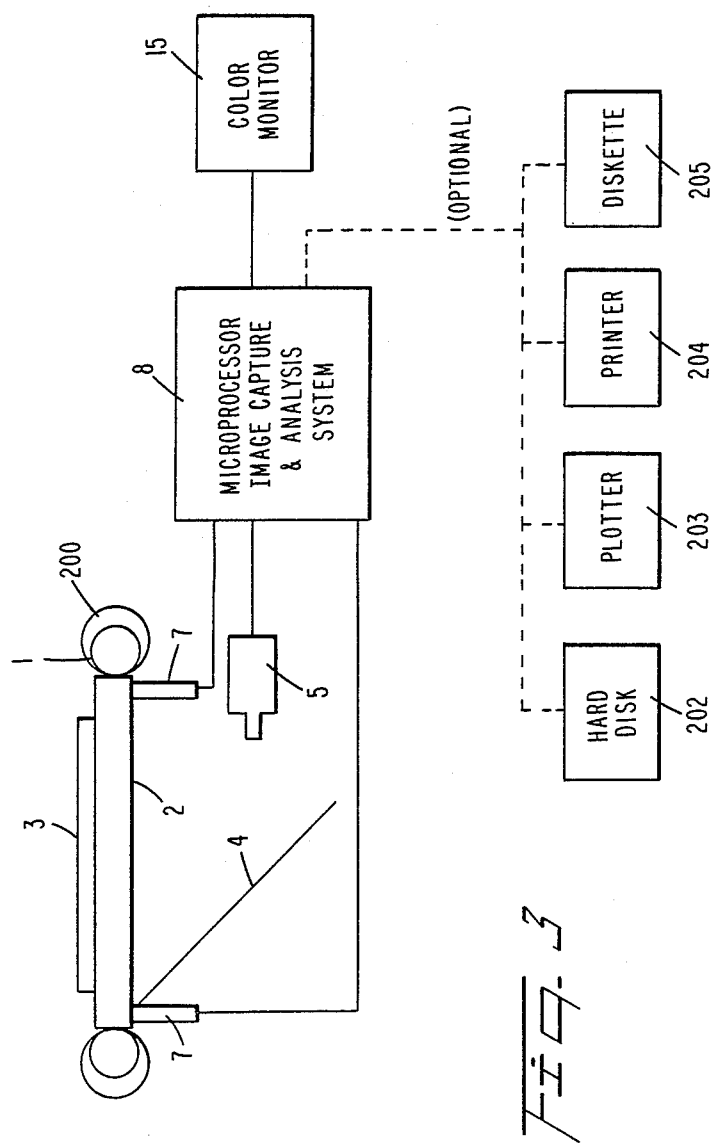

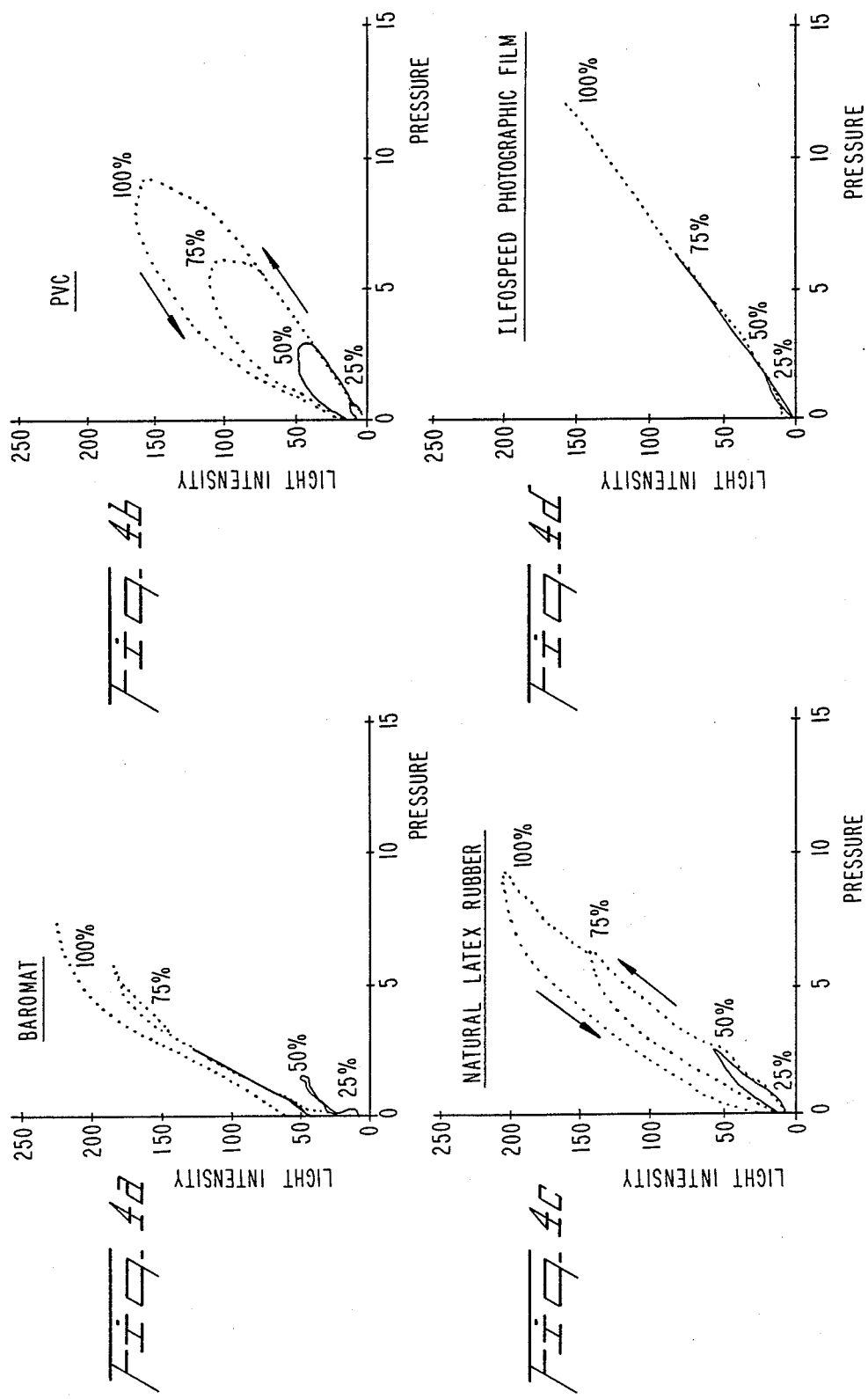

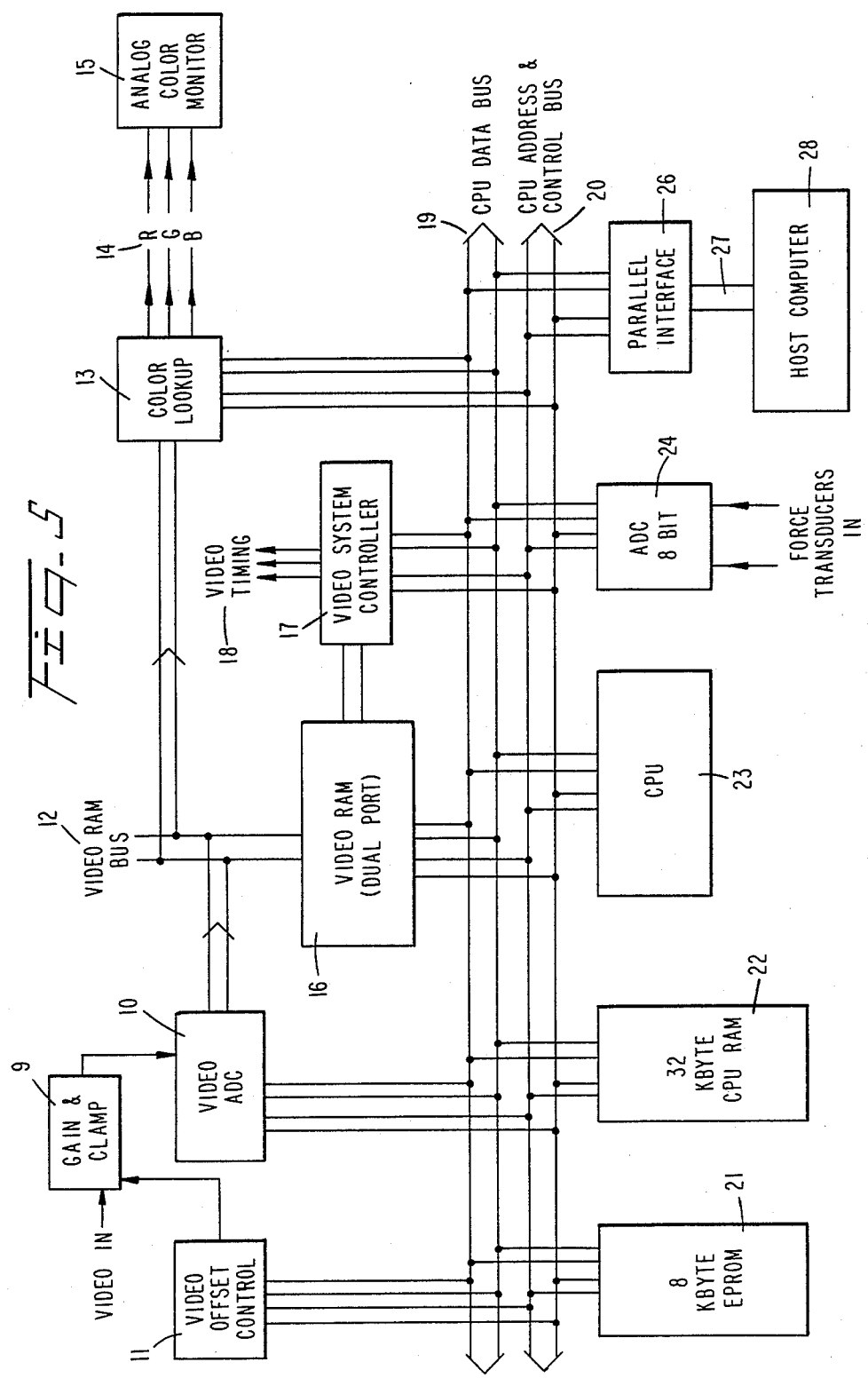

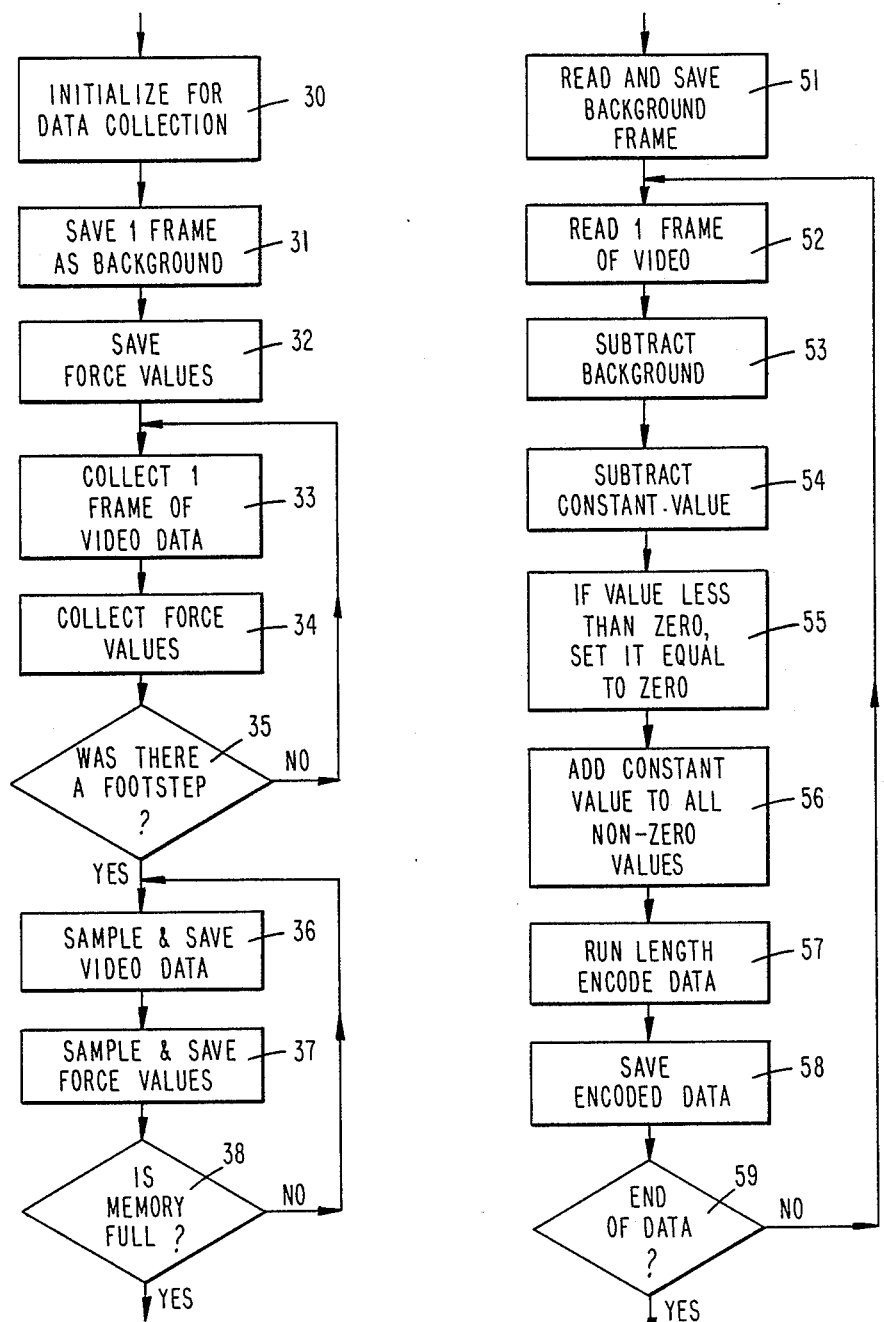

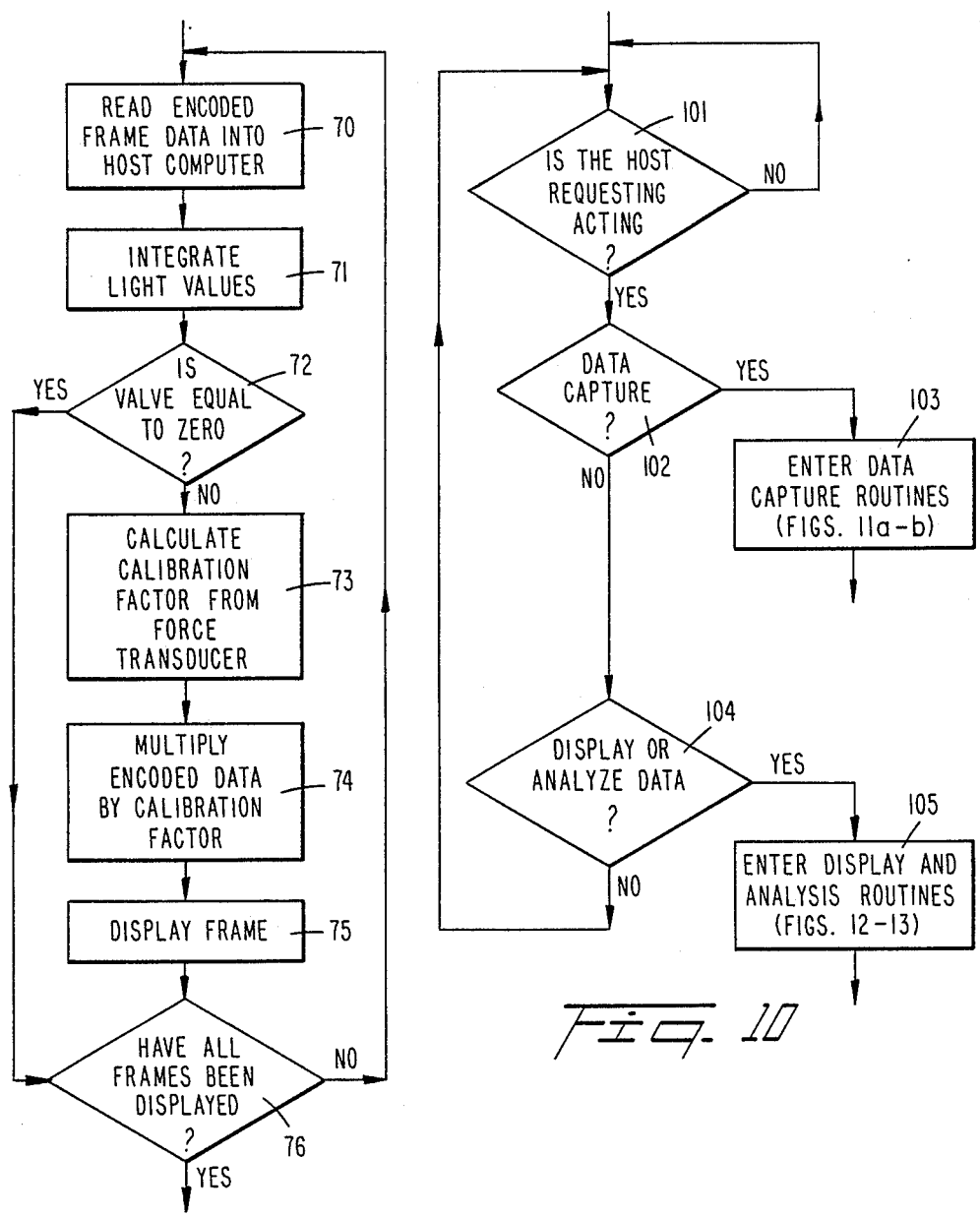

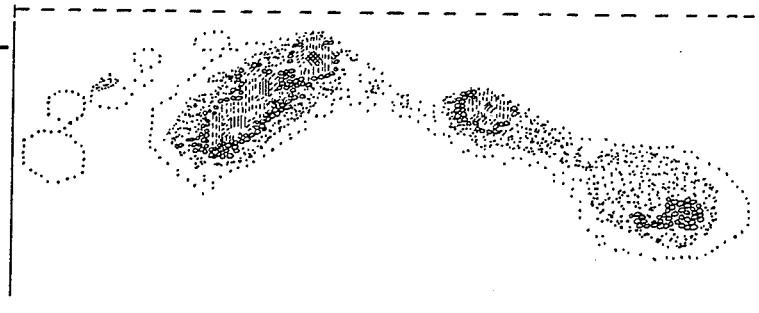
Fig. 9d
t = 0.23 SEC
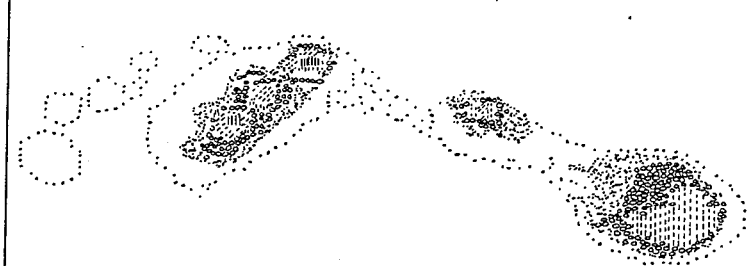
Fig. 9c
t = 0.17 SEC
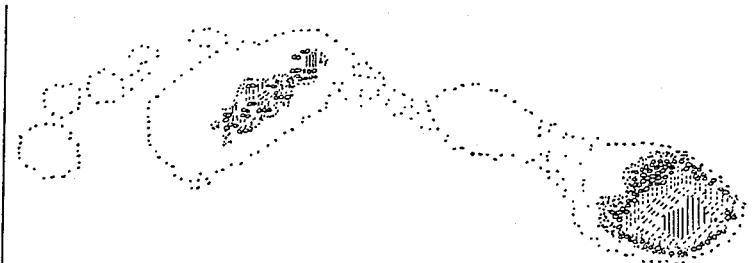
Fig. 9b
t = 0.10 SEC
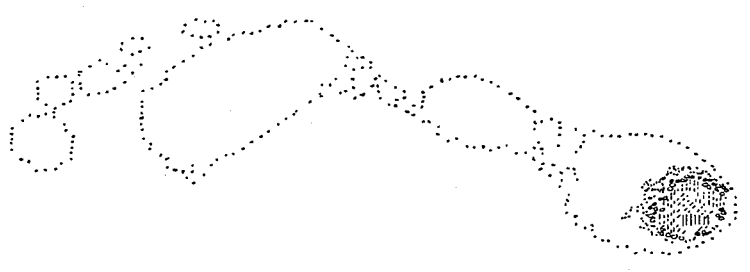
Fig. 9a
t = 0.03 SEC

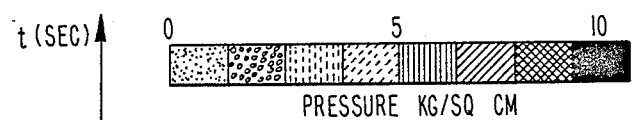
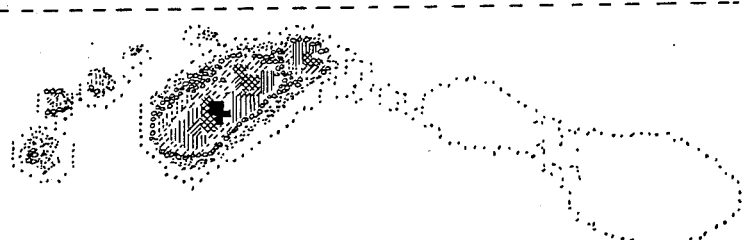
Fig. 9h
t = 0.50 SEC
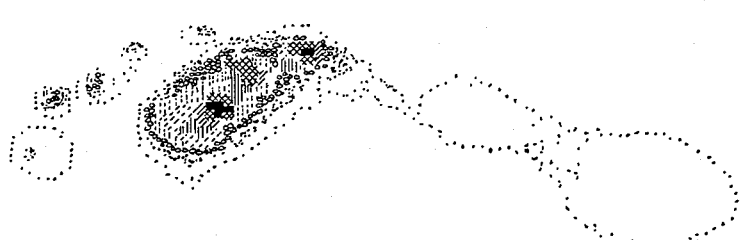
Fig. 9g
t = 0.43 SEC
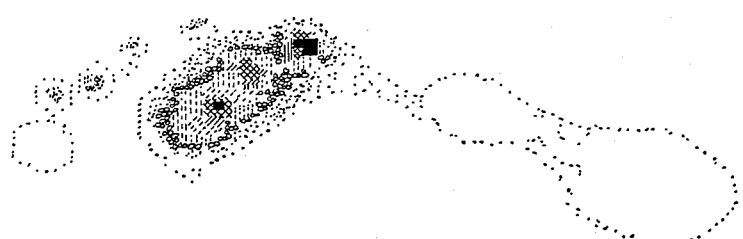
Fig. 9f
t = 0.37 SEC
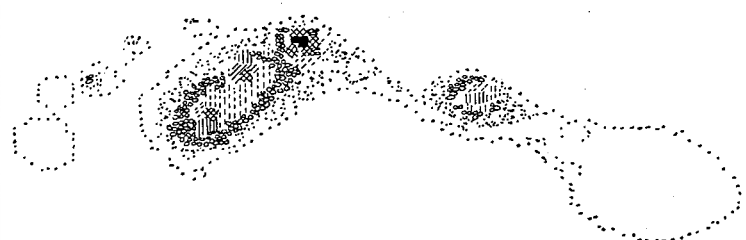
Fig. 9e
t = 0.30 SEC

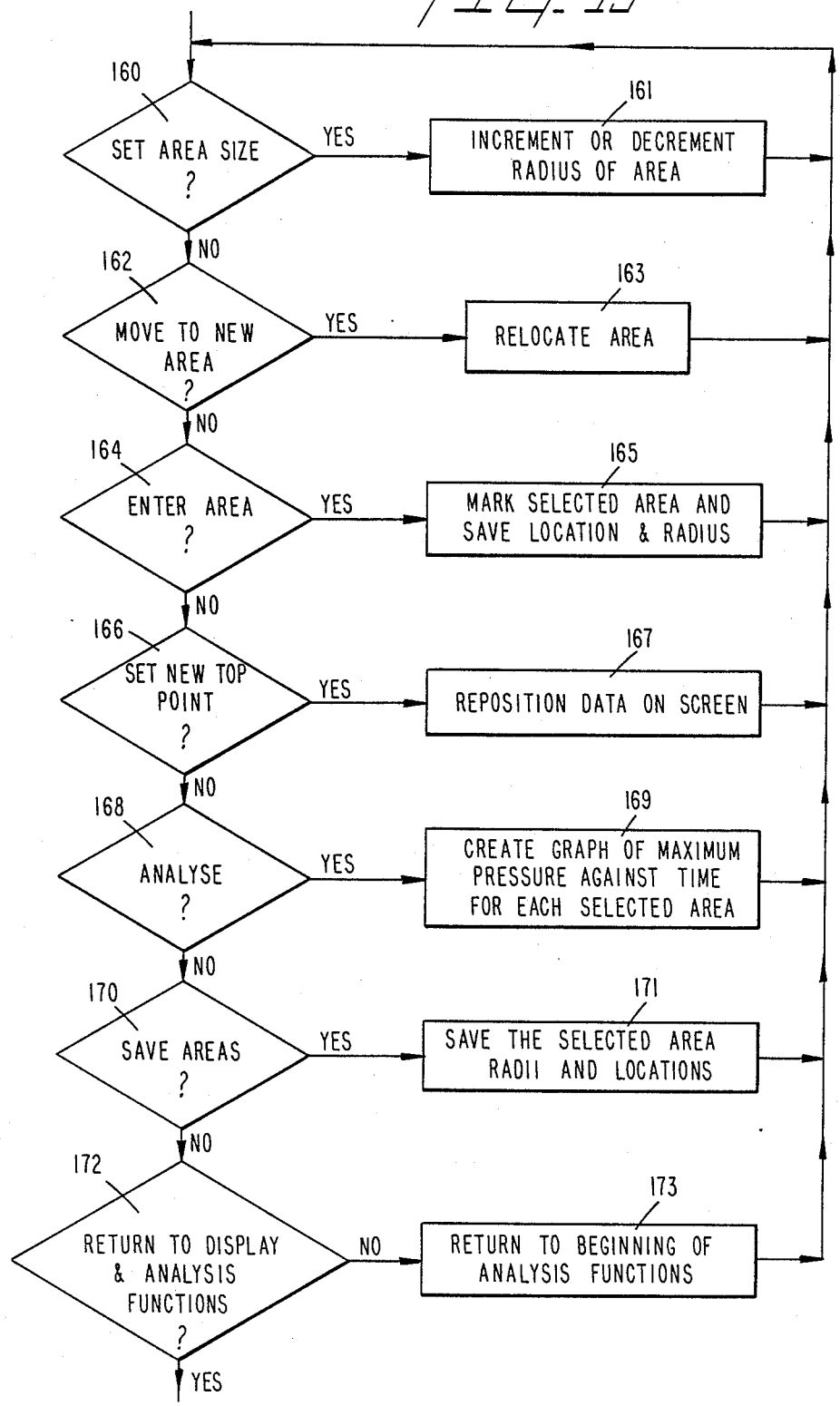

FOOT PRESSURE MEASUREMENT SYSTEM

BACKGROUND OF THE INVENTION

This invention relates to the field of pressure measurement. Specifically this invention relates to an improvement in an optical technique for pressure measurement used in the field of static and dynamic foot pressure distribution measurements.

One prior art foot pressure measurement system is disclosed in R. P. Betts and T. Duckworth, "A Device for Measuring Plantar Pressures Under the Sole of the Foot," 7 Engineering in Medicine 223 (1978). As described therein, this system comprises a glass or transparent plate illuminated along two or more edges, with a thin sheet of reflective material on its upper surface, as shown in FIGS. 1 and 2. The light shining into the plate normally is internally reflected. The reflective material causes light to escape through the top and bottom surfaces of the glass plate when pressure is applied to the reflective material. The amount of light escaping is proportional to the applied pressure. Viewing the underside of the glass reveals the applied pressure distribution as a variation in light intensity. The variation of light intensity and hence pressure are conveyed to the observer by viewing the underside of the plate, either directly or using a mirror, with a monochrome television camera. In an alternative prior art embodiment, the reflected light is processed into color bands for a display on a color monitor, each band representing a specific pressure range.

A significant advance in this art was made by capturing the light intensity data in a computer system. See. e.g., C. I. Franks, et al., "Microprocessor-based Image Processing System for Dynamic Foot Pressure Studies," Medical & Biological Engineering and Computing 566 (Sept. 1983). A typical configuration for such a system is shown in FIG. 3. In this system data from the video camera is converted into digital format by a microprocessor image capture and analysis system, and the data are stored in digital memory. This system enables the observer to playback the pressure distribution data from either a static or dynamic sequence of samples and to perform further analysis of the data. With the development of this system improved calibration techniques became possible and were implemented by measuring the total vertical force applied to the top surface of the plate each time light intensity distribution was measured using force transducers. This provided the necessary data with which to calibrate the light values in terms of applied pressures.

The prior art systems depend on distinguishing background light levels from light levels caused by foot pressure by setting a threshold level, below which all light values are considered to be background light. As there is a certain amount of noise in the video data, and a degree of irregularity in the evenness of background light escaping from the glass plate, setting a threshold level can lead to loss of low levels of foot pressure data if the threshold level is set too high and erroneous data if the threshold level is set too low.

SUMMARY OF THE INVENTION

Accordingly, one object of the present invention is to provide an improved foot pressure measurement system with a variable background threshold level.

Another object of the present invention is to provide an improved foot pressure measurement system in which background threshold levels may be made to correspond to each element of the scanned view of the light output.

Another object of the present invention is to enable detection of lower pressure levels in a foot pressure measurement system than otherwise would be possible.

A further object of the present invention is to eliminate or substantially reduce interference caused by variations in the amount of light escaping from the glass plate in a foot pressure measurement system.

A still further object of the present invention is to eliminate or substantially reduce in a foot pressure measurement system the effect of increased or decreased light value levels escaping from the glass plate as a result of internally reflected images which may be seen through the underside thereof.

Another object of the present invention is to compensate in a foot pressure measurement system for increased or decreased light levels escaping from the glass plate as a result of impurities within the glass.

A further object of the present invention is to compensate for increased or decreased light values escaping from the glass plate in a foot pressure measurement system as a result of foreign objects within the glass.

A still further object of the present invention is to capture and store in a foot pressure measurement system variable background threshold data immediately prior to capturing pressure data.

Another object of the present invention is to reduce the effect on the emission of background light from the glass plate in a foot pressure measurement system caused by changes in ambient temperature.

A further object of the present invention is to eliminate the effects of long term fluctuations in light intensity from glass plate 2 of a foot pressure measurement system.

A further object of the present invention is to eliminate the effects of medium term fluctuations in light intensity from the glass plate of a foot pressure measurement system.

Another object of the present invention is to eliminate calibration errors caused by variations in background light levels from the glass plate of a foot pressure measurement system.

A still further object of the present invention is to enable effective run length encoding of data and hence reduced storage space requirements by eliminating background light levels in a foot pressure measurement system.

Another object of the present invention is to provide an improved reflective material in a foot pressure measurement system.

Briefly, in accordance with the preferred embodiment of this invention, the foregoing objects are achieved by providing an improved foot pressure measurement system in which a reference measurement is made of background light intensity and distribution before pressure is applied to the reflective material on the glass plate and this background light intensity is subtracted from the light levels when pressure is applied. A photographic paper is used as the reflective material on the top surface of the glass plate to improve the reflectance characteristics of the system.

BRIEF DESCRIPTION OF THE DRAWINGS

FIG. 1 is a diagram of the optical portion of the prior art foot pressure measurement system which is incorporated in the present invention.

FIG. 2 is an enlarged view of the reflective material-to-glass interface of the prior art foot pressure measurement system.

FIG. 3 is a diagram of the prior art microprocessor-based dynamic foot pressure measurement system, with force transducers at the corners of the glass plate.

FIGS. 4a–d are graphs of the light intensity versus applied pressure for various types of reflective materials.

FIG. 5 is a block diagram of the microprocessor image capture and analysis system of the present invention.

FIG. 6 is a flow chart showing data collection in the present invention.

FIG. 7 is a flow chart showing background reduction and data encoding in the present invention.

FIG. 8 is a flow chart showing data calibration and display in the present invention.

FIG. 9 is an illustration of output foot pressure printout of the present invention showing some of the sequential frames of data.

FIG. 10 is a flow chart of the control program's primary functions of the present invention.

FIG. 13 is a flow chart of the analysis functions in the control program of the present invention.

DETAILED DESCRIPTION OF THE PREFERRED EMBODIMENT

Figure 11A:
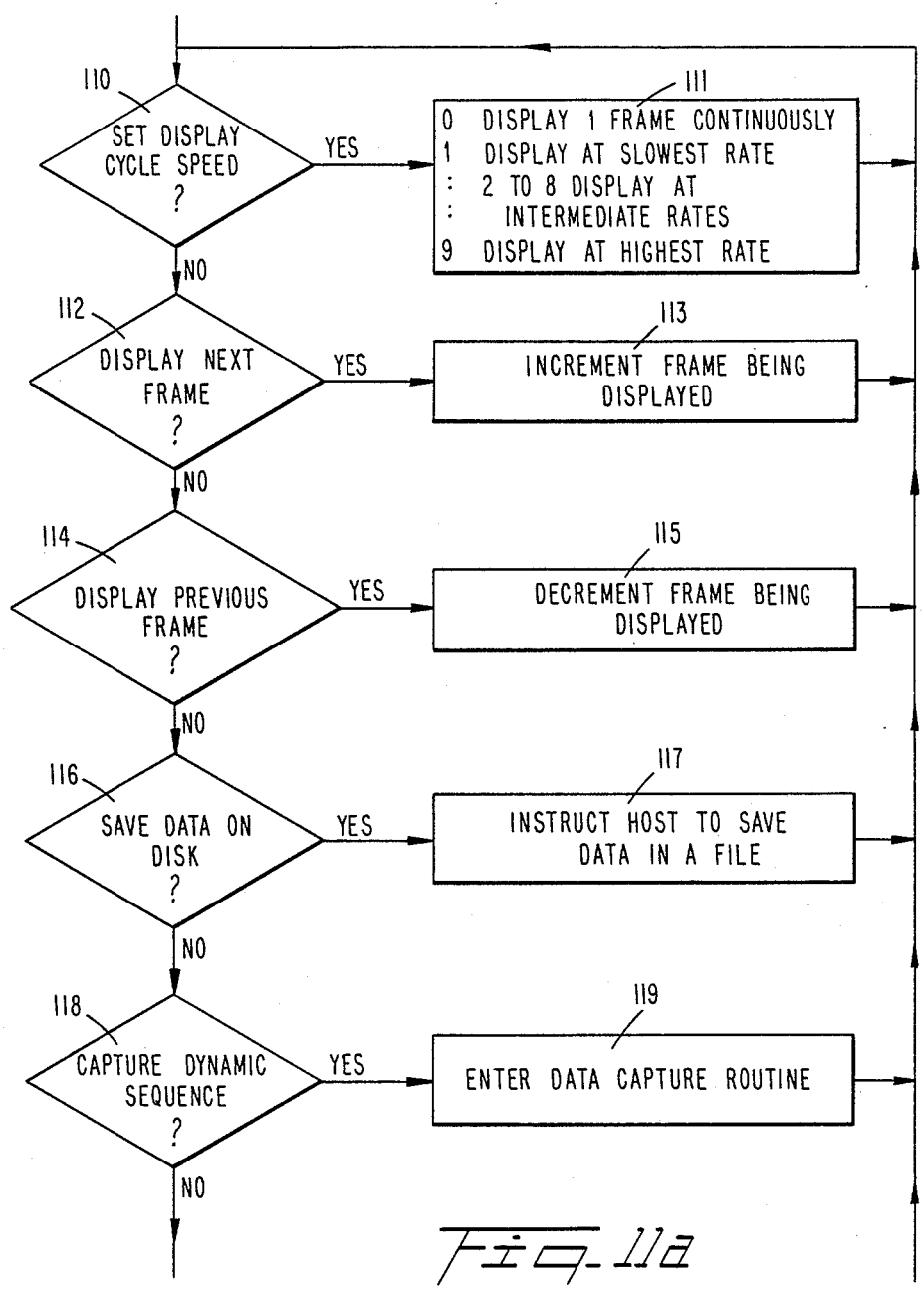
FIGS. 11a–b are flow charts of the data capture functions in the control program of the present invention.

Referring now to the drawings wherein like referenced numbers designate identical or corresponding parts throughout the several views, FIG. 1 illustrates the optical portion of the prior art foot pressure measurement system incorporated in the present invention.

In the preferred embodiment, glass plate 2 is made of Pilkington clear white plate glass, grade A, measuring approximately 22.5 inches by 19 inches by 1 inch. Other suitable materials are plexiglass and Dow Corning Pyrex. The surfaces and edges of glass plate 2 are ground flat and polished to ensure maximum transmission of light and to minimize spurious reflections.

Conventional fluorescent strip lights 1 are mounted so as to allow light only to penetrate the edge of glass plate 2. The strip lights are mounted inside conventional reflectors 200. A sheet of reflective material 3 is positioned on the top surface of glass plate 2. A mirror 4 is positioned beneath glass plate at a 45° angle thereto. The lens of monochrome television camera 5 is focused on mirror 4 and is aimed along an axis parallel to the surface of glass plate 2.

FIG. 2 illustrates the interface between glass plate 2 and reflective material 3. In FIG. 2a, no pressure is applied to this material. Because of the irregular surface of reflective material 3 there are numerous air gaps separating it from glass plate 2. Since air has a lower refractive index than glass, light passing through glass plate 2 from strip light 1 is internally reflected where air gaps exists between glass plate 2 and reflective material 3. Where reflective material 3 comes into intimate contact with glass plate 2, such as at point 201, internal reflection does not occur because reflective material 3 has a higher refractive index than glass. At these points of contact light is refracted out of the glass and scattered back in all directions from the surface of reflective material 3. A portion of the scattered light is reflected through the bottom surface of glass plate 2 to mirror 4 and into television camera 5.

Referring to FIG. 2b, when pressure is applied to reflective material 3, such as by a person standing on the upper surface thereof, the deformable surface of this material is forced into more intimate contact with the upper surface of glass plate 2, the total area of such contact depending on the applied pressure. Output light intensity versus applied pressure for a variety of different reflective materials in shown in FIGS. 4a–d. In each curve the 25th, 50th, 75th and 100th percentile curves are shown for the corresponding reflective material. These percentiles refer to pixels having a light intensity at the specified percentile level. For example, the 75th percentile curve means that the pressure versus light intensity curve is for pixels having a sufficiently high light intensity that 75% of the total pixels have a lower light intensity while 25% have a higher light intensity. FIG. 4a illustrates the pressure versus light sensitivity curve for "Baromat" ridged surface silicone rubber manufactured by Biomechanics of La Mesa, Calif. FIG. 4b illustrates the pressure versus light sensitivity curve for white polyvinyl-chloride, trade named "Velbex" manufactured by Storeys Industrial Products, Ltd. FIG. 4c illustrates the pressure versus light sensitivity curve for natural latex rubber, grade "S" manufactured by Four D Rubber Co., Ltd. FIG. 4d illustrates the pressure versus light sensitivity curve for a resin coated photographic paper, trade named "Ilfospeed," No. MG.44M, medium weight pearl finish, manufactured by Ilford, S.A.

Baromat, PVC plastic and natural latex rubber, as shown in FIGS. 4a–c, respectively, have been used in prior art foot pressure measurement systems. As these figures show, the pressure versus light intensity curves are nonlinear. Furthermore, in the case of PVC and natural latex rubber, the pressure versus light intensity curves exhibit hysteresis, i.e., the light intensity follows one curve when pressure is increased from zero to a specified maximum level and then follows a different curve as pressure is removed from the material. As shown in FIG. 4d, the resin coated photographic paper exhibits an essentially linear pressure versus light intensity curve and exhibits no hysteresis. This material also shows little viscoelasticity, tackiness or other hesteresis-like effects and exhibits no evidence of saturation over the pressure range studied.

Referring again to FIG. 1, the upper surface of reflective material 3 is covered by an opaque material 6, such as a photographic dark room rubberized fabric. The preferred reflective material is resin coated photographic paper, such as the "Ilfospeed" photographic paper discussed in connection with FIG. 4, which should be "fixed" by the normal photographic developing process and placed white side down on the upper surface of glass plate 2. The same type of photographic paper is also manufactured by Kodak and is identified as "Poly Contrast" paper. An alternative reflective material is trade named "White Colour Card," 0.013 inch thickness, manufactured by Slater-Harrison.

Referring to FIG. 3, glass plate 2 is mounted on force transducers 7 placed at each of the four corners thereof.

These transducers measure the overall vertical force applied to glass plate 2, allowing a highly accurate calibration of the relationship between light levels and pressure. In an alternative embodiment, multi-component force transducers are used which also measure shear forces and torques applied to glass plate 2. This increases the versatility of the pressure measurement system of the present invention in some applications. The optical axis of camera 5 is parallel to glass plate 2. To reduce the overall height of the structure of this system, mirror 4 and camera 5 may be rotated as a unit so that the angle between mirror 4 and glass plate 2 is reduced to less than 45°. It is essential, however, that the angular relationship between mirror 4 and camera 5 remain constant to maintain the correct view of the underside of glass plate 2.

For optimum results the entire structure shown in FIG. 1 (with the exception of the top surface of glass plate 2 which is already covered by reflective material 3, which is in turn covered by opaque material 6) is enclosed in a light proof assembly to exclude extraneous light from glass plate 2, mirror 4 and camera 5. Camera 5 may be positioned externally to the light-proof assembly, with provision made for the camera lens to view mirror 4 through an aperture in the light-proof assembly.

Using the resin coated photographic paper as the reflective material 3 of the preferred embodiment, video camera 5 generates an output analog signal whose magnitude is directly proportional to the pressure exerted on this film.

Referring again to FIG. 3, the output signal from monochrome TV camera 5 is input to microprocessor image capture and analysis ("MICA") system 8. MICA system 8 is shown in block diagram form in FIG. 5. Also input to MICA system 8 are the output signals generated by each of the force transducers 7. The video signal from video camera 5 is input to a conventional gain and clamp circuit 9, such as the combination of an Analog Devices Model No. AD711 operational amplifier (gain) and a Burr Brown Model No. SHC298 (sample and hold). Gain and clamp circuit 9 is controlled by a standard video offset control ("VOC") circuit 11, such as an Analog Devices Model No. AD558. CPU 23 provides data value to VOC 11, which is determined by integrating the digital video signal from a single frame from camera 5 and comparing this integrated light value to a preselected value. If the integrated light value exceeds the preselected value, VOC 11 increases the offset voltage fed to gain and clamp circuit 9; conversely, if the integrated light value is less than the preselected value, VOC 11 decreases the offset voltage fed to gain and clamp circuit 9. The output of gain and clamp circuit 9 is input to a conventional high-speed video analog to digital converter ("ADC") 10, such as a Micro Power Model No. MP7684.

The operation of MICA system 8 is controlled by a conventional central processing unit ("CPU") 23, which may be an 8, 16 or 32 bit processor or any other device capable of being programmed and of providing control functions for the other components of the system. In the preferred embodiment CPU 23 is a Harris Model No. 80C88 microprocessor. CPU 23 passes and receives data to and from the other elements of the system via conventional CPU data bus 19. Similarly, device and memory addresses, control signals, requests and acknowledgements are transmitted between CPU 23 and the other system elements via CPU address and control bus 20.

In the preferred embodiment, video ADC 10 converts the analog video signal for each pixel in video camera 5 into an 8 bit digital value. The digital output from video ADC 10 is fed onto a conventional video random access memory ("video RAM") bus 12, as described below, by means of a signal from CPU 23 on CPU address and control bus 20.

The digital values produced by video ADC 10 are stored in a conventional video random access memory ("video RAM") 16, such as a Fujitsu Model No. MB 8146115. Data is input to video RAM 16 on video RAM bus 12 under control of a conventional video system controller 17, such as a Texas Instruments Model No. TMS 34061. Video RAM 16 can store 1,048,576 bytes, or 32 frames of video data, each of which measures 256 pixels by 128 pixels. Video system controller 17 provides video timing and synchronizing signals 18 for the video elements of the system, such as horizontal and vertical sync pulses and horizontal and vertical blanking pulses.

The 8-bit digital values produced by video ADC 10 are also input to a conventional color lookup device 13, such as an Inmos Ltd. Model No. IMS G170S50, which converts these values into three analog values to drive the red, green and blue inputs 14 to a conventional analog color graphics monitor 15 such as an NEC Multisync. This produces a color-coded display of the pressure data seen by monochrome video camera 8. In this way the pressure values are grouped into bands of colors for easier recognition by the user of the present system. Color lookup device 13 is preset by CPU 23 to provide a selected range of colors at its output. It has 256,000 colors to choose from, of which a palette of 256 may be selected at any one time. For example, if the digital value 15 is input to color lookup device 13, the color light blue is generated, while if the digital value 30 is input, the color dark blue is generated.

Video RAM 16 is dual-ported to allow simultaneous access to its data by video system controller 17 and CPU 23. In this way, CPU 23 may access the digitized video data while it is being input to video RAM 16.

Programming information for CPU 23 is stored in a conventional 32 kilobyte random access memory 22 ("CPU RAM"), such as an NEC Model No. D43256C-12L. This memory contains the CPU control program and various constants such as values for color lookup device 13 and VOC 11.

Referring again to FIG. 3, each of the force transducers 7 generates a voltage directly proportional to the force exerted on glass plate 2. As shown in FIG. 5, these signals are fed to a conventional analog to digital converter ("ADC") 24, such as Analog Devices Model No. AD7828, which converts these analog voltages into 8-bit digital format. The output of ADC 24 is fed to CPU RAM 22. In the preferred embodiment four force transducers are used so that four 8-bit digital channels are output from ADC 24. It should be understood, however, that a larger number of force transducers may be used in the instant invention.

In the preferred embodiment control programs, described below are transferred from and data are transferred to and from a host computer 28, such as an IBM Model PC/AT, via a conventional parallel interface 26, such as an Advanced Micro Devices Model No. 82C55, communicating over bus 27. This provides flexibility in programming and operation of the system. In an alternative embodiment, the entire system of FIG. 5 is incorporated into host computer 28 itself. In another alternative embodiment the entire system of FIG. 5 (excluding host computer 28 and monitor 15) is incorporated in a single integrated circuit board, such as the True Vista Video Graphics board, Model AT Vista, made by True Vision, Inc.

A conventional "bootstrap" program is stored in eight kilobytes of a conventional erasable programmable read-only memory ("EPROM") 21, such as an Hitachi HN27C64G-15, to enable system operation to begin. On "power up" the bootstrap program sends a reset pulse through the system to initialize all of the component elements. This program then directs CPU 23 to input or "download" the control program and certain system parameters, described below, from host computer 28 through parallel interface 26.

In the preferred embodiment host computer 28 is programmed to calculate calibration values from the force and video data, as described below. CPU 23 may also be programmed to modify the video data, as described below. Host computer 28 interacts with CPU 23 providing it with information to display, via video RAM 16 and color lookup 13, on a conventional analog color monitor 15, such as an NEC "Multisync" monitor. Similarly, the initiation of data collection from both video ADC 10 and 8-bit ADC 24 may be ultimately controlled by host computer 28. Data collected by the instant pressure measurement system may be stored and further processed, if desired, by host computer 28.

Operation of the system is explained by reference to the flowcharts in FIGS. 6-8. As shown by block 30 in FIG. 6, the system is initialized for data collection by the "bootstrap" program which downloads program instructions and constant data parameters, such as the video offset control parameters, color lookup parameters and video system controller parameters, from host computer 28. After initialization one frame of video data is input from monochrome television camera 5 to MicaSystem 8, prior to any pressure being applied to glass plate 2. This provides background level data for each pixel sample. A video frame in the instant system comprises a field of 128×256 pixels or 32,768 pixels per frame. The video signal for each pixel is converted by video ADC 10 into an 8-bit digital word and stored in video Ram 16, as shown by block 31 in FIG. 6.

After the video background frame has been stored, the voltages generated by force transducers 7 are sampled and converted into 8-bit digital words by ADC 24. This data is stored in CPU RAM 22 as baseline data, as shown by block 32.

The program then enters a loop wherein the next frame of video data is observed by video camera 5, digitized by video ADC 10 and stored in video RAM 16, as shown by block 33. The force transducer data from force transducers 57 are then sampled by ADC 24 during transmission of the first video frame, as shown in block 34. The video data stored in video RAM 16 is compared with the previously stored video data for the background frame by subtracting the digital value for each pixel in the background frame from the digital value for the corresponding pixel in the video frame. These differences are then summed. If the sum is greater than a specified threshold value, input from host computer 28, it is assumed that pressure has been applied to glass plate 2. Alternatively, the same type of comparison is made between the stored baseline reference level of force transducers 7 (block 32) with the new values for these transducers (block 34) and an increase in level above a specified threshold level indicates an increase in pressure applied to glass plate 2. Block 35 illustrates this step. This pixel-by-pixel comparison is carried out as pixel data for the current frame is read into video RAM 16 by means of the dual port in this device.

If there is no change in pressure levels (either by comparing the background video frame against the current video frame or by comparing the baseline force transducer data against the current force transducer data), this process is reiterated. Thus, the next frame of video data is input to video RAM 16 and compared with the background frame, and the next corresponding set of force transducer data is input to CPU RAM 22 and compared with the baseline data. During this repetitive sequence the data in video RAM 16 for the current frame writes over the data for the preceding frame and the current force transducer data in CPU RAM 22 corresponding to the preceding frame writes over the force transducer data for the frame.

If the comparison between the background frame and the current frame indicates a change in pressure level above the specified minimum, or if the comparison between the baseline force transducer data and the current force transducer data indicates a change in pressure level on glass plate 2, the system proceeds to the loop defined by blocks 36–38 in FIG. 6. The first step, as shown by block 36, is to sample and save the current video frame. This frame is stored in a separate location in video RAM 16. Similarly, the current set of force transducer data, as shown in block 37, is sampled and stored in a separate location in CPU RAM 22.

The system then interrogates to determine whether video RAM 16 is full, i.e., whether it has stored 32 frames of video data, as shown by block 38. If video RAM 16 is not full, the system returns to block 36 and repeats this process for the next frame of video data and force transducer data. This process continues until video RAM 16 is full, i.e., it contains 32 frames of video data. Since a footstep typically does not last for the duration of all 32 frames, there will be one or more frames stored in video RAM 16 which contain only background data and one or more corresponding sets of force transducer data stored in CPU RAM 22 comprising baseline reference data.

Referring now to FIG. 7, the background video frame, which previously had been used to determine initiation of a footstep and the first frame of video data stored in video RAM 16 containing foot pressure data are read by CPU 23 on a pixel-by-pixel basis, as shown in blocks 51 and 52. Each background video frame pixel is subtracted from the corresponding first frame pixel, as shown in block 53. This subtraction has the effect of reducing background levels to very low digital values, such as 1 or 2, depending on the short-term noise in the system. This step is followed by subtracting a constant value, such as digital 3, from each pixel value, as shown in block 54. If the resulting pixel value is negative, it is set to zero, as shown in block 55. As a result of this step, a zero pixel value indicates no pressure has been applied to the area in glass plate 2 corresponding to this pixel, while a non-zero pixel value indicates that pressure has been applied to this area. The constant value used in block 54 is then added back to the non-zero pixel values, as shown in block 56. The background-free video data is then written over the unmodified data in video RAM 16. The result of this process is that the background signal (corresponding to the absence of pressure from a footstep) is eliminated from the video signal on a pixel-by-pixel basis.

The modified data in video RAM 16 may then be compressed, as shown at block 57, to reduce storage space requirements using standard data compression techniques. For example, because the background data has been set to zero, an effective method of data compression is to "run length encode" the data. Using this technique two numbers are used to represent a stream of constant values. The first number indicates the data value and the second number indicates how many times the data value is repeated. In this way, long streams of unchanging values are reduced to two data values for storage. For example, if one line of the video frame had foot pressure at locations on glass plate 2 corresponding to the first ten pixels of a particular video scan line and there was no foot pressure at locations corresponding to the remaining 118 pixels in that line, this data could be run length encoded by storing the numbers "0" and "118."

The encoded data is then saved in CPU RAM 22, as shown by block 58. The program then checks to see if all stored frames have been processed, as shown in block 59. If additional frames must be processed, the system loops back to block 52 and the next video frame is read and compared with the background frame, in the same manner as above. If no further video frames are to be processed, the system exits to the series of steps illustrated in block diagram form in FIG. 8.

Referring now to FIG. 8, the video data is calibrated in host computer 28 following the encoding process. The first frame of encoded data is read from CPU RAM 22 into host computer 28 through parallel interface 26, as represented by block 70. The light values are then integrated over the entire video frame, i.e., the digital values for all pixels are added together for the entire frame, as represented by block 71. The integrated value is then tested to determine if the frame contains any pressure data, as shown by block 72. If the integrated value is zero (indicating that the frame has no pressure data), the system skips to block 76, whose function is described below. If the integrated value is non-zero (indicating that the frame has pressure data), the frame data is calibrated.

The calibration factor for a frame is calculated from the following equation, as represented in block 73:

$$C = F / \left( A_p \times \sum_{i=1}^{N} L_i \right)$$

where
$L_i$ light value (0–255) for the "i"th pixel,
N = number of pixels
$A_P$ = pixel area
F = total force on glass plate 2
C = calibration factor (same for all pixels)

Pixel area is calculated from the geometrical relationship between the camera scan area and the dimensions of the viewed area of glass plate 2. It may be found by applying points of pressure at known separations on glass plate 6 and then identifying the corresponding pixels in the video output. For example, if pressure is applied to two points on glass plate 2, separated by ten inches and this pressure generates increased light values at pixels 20 and 120 on a particular scan line, the pixel separation equals 100 and adjacent pixels correspond to a 0.1 inch separation on glass plate 2.

Force in the foregoing calibration equation is determined by adding the four digitized values for the output of force transducers 7 corresponding to the video frame being calibrated. As described above, this data is stored in CPU RAM 22.

Every pixel for the particular frame being calibrated is then multiplied by the calibration factor, as shown by block 74. After the frame data has been calibrated it is fed to color lookup device 13, which generates an analog voltage corresponding to the calibrated digital value for each pixel. Since the pixel value is encoded in an eight-bit word, color lookup device 13 generates 256 different combinations of analog voltages on the "R" (red), "G" (green) and "B" (blue) output lines 14. The output of color lookup device 13 is fed on lines 14 to color monitor 15, which displays the video frame in color from a palette of 256 colors, as represented by block 75. Alternatively, as shown in FIG. 3, the output of color lookup device 13 may be fed to a printer 204, a plotter 205, or stored on a hard disk 202 or a diskette 205. An example of eight frames printed by printer 204 showing foot pressure at times 0.03, 0.10, 0.17, 0.23, 0.30, 0.37, 0.43 and 0.50 seconds are shown, respectively, in FIGS. 9a–h. As shown in FIG. 9a, the foot begins exerting pressure at the heel. Pressure then is applied to the ball of the foot (FIGS. 9b–d). As pressure is removed from the heel, it begins to be applied to the smaller toes (FIGS. 9e–f) and finally is applied to the large toe (FIGS. 9g–h).

Referring again to FIG. 8, the system interrogates to determine whether all frames have been displayed, as shown by block 76. If additional frames remain to be displayed the system loops back to block 70 and performs the same sequence of steps for the next frame. When all frames have been displayed, the system exits this loop.

Flow charts for a typical control program for CPU 23 are shown in FIGS. 10–13. Referring first to FIG. 10, the program is entered at 100. CPU 23 interrogates parallel interface 26 to see if the host computer 28 is requesting action. If no action is requested the control program continues to interrogate parallel interface 26. If host computer 28 requests action the control program evaluates the request, as shown by block 102 to see if it should enter the data capture routines in FIGS. 11a–b. If this action is required, the data capture routines, described below, are entered as shown at block 103. If the data capture routines are not required the control program tests to see if it should enter the display and analysis routines in FIGS. 12–13. If this action is required the display and analysis routines, described below, are entered, as shown at block 105. If neither of these actions is required, the control program returns to block 100 and monitors the parallel interface for further requests from host computer 28.

Figure 11B:
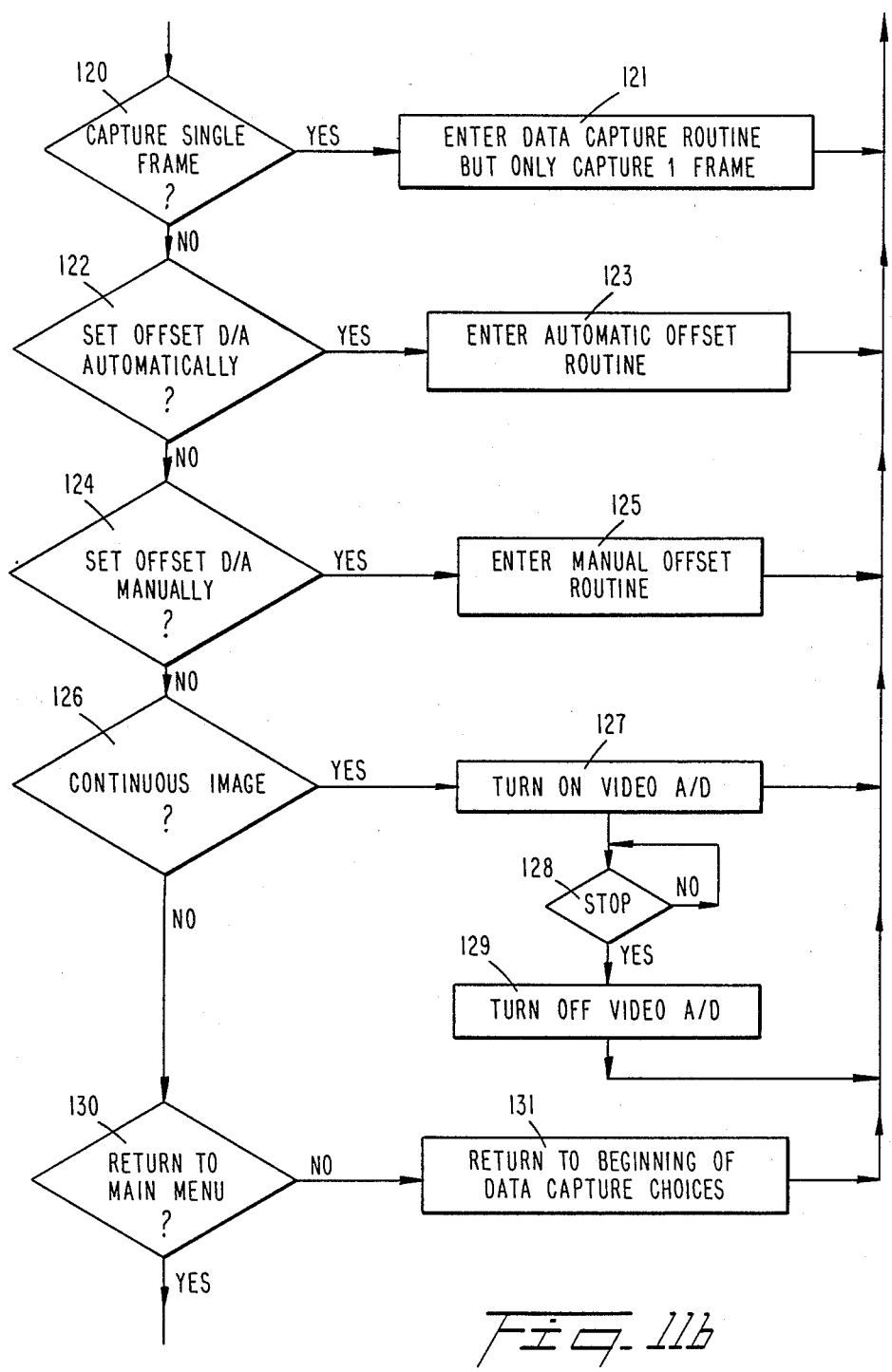

A flow chart indicating the data capture functions is shown in FIGS. 11a–b. This portion of the control program allows the operator to direct CPU 23 to carry out various functions, as described below.

Function 110 ("Set Display Cycle Speed?"): This function controls the repetition rate for displaying the sequential samples of pressure data. As shown in block 111, the operator inputs a value between 0 and 9 from host computer 28. A value of 9 selects the highest possible display rate, while progressively lower values slow the rate down. The value of 0 "freezes" the display at the currently displayed frame.

Function 112 ("Display Next Frame?"): This function is selected by the operator by inputting a space character from host computer 28. This selects the next frame in sequence, as shown at block 113, allowing the operator to step through the display of sequential pressure data (when used in combination with the frame display rate value 0).

Function 114 ("Display Previous Frame?"): This function is selected by the operator inputting the minus character from host computer 28. This causes the displayed frame to be decremented (block 115), allowing the operator to step backwards through the display of sequential pressure data (when used in combination with the frame display rate value 0).

Function 116 ("Save Data on Disk?"): When the host computer requests this function pressure data from video RAM 16 is transferred via parallel interface 26 to host computer 28, which stores the data in a file on hard disk 202 or diskette 205. The values for the force transducer data are also transferred and saved, simultaneously.

Function 118 ("Capture Dynamic Sequence?"): When the host computer requests this function the data capture routines previously described in FIG. 6 are entered, and a sequence of pressure events is sampled and stored in video RAM 16.

Function 120 ("Capture Single Frame?"): When host computer 28 requests this function the data capture routines are entered but capture is limited to a single frame of data from video camera 5.

Function 122 ("Set Offset D/A Automatically?"): When host computer 28 requests this function a routine is entered which sets video offset control 11 as follows: Video offset control 11 is loaded with a default value and one frame of video data is acquired and stored in video RAM 16. This video data is then transferred to host computer 28 which integrates the light values. The resulting integral is then compared with a pre-defined target value. If the integral has a higher value than the target value, video offset control 11 is reset with a new, increased value to raise the video offset voltage. This voltage is applied to gain and clamp circuit 9, which adjusts the level of video voltage applied to video ADC 10, such that background video levels are reduced. If the integral has a lower value than the pre-defined target level, video offset controller 11 is reset with a lower value. After the video offset voltage is reset a new frame of video data is acquired and the process is repeated. This procedure continues until the integrated light from the video field is within a predetermined margin of the target value.

Function 124 ("Set Offset D/A Manually?"): This function allows the operator to load video offset control 11 with a value from host computer 28. The level of video background may thus be preset directly by the operator.

Function 126 ("Continuous Image?"): If this function is selected by host computer 28, video ADC 10 will be turned on (block 127). This passes the video data directly through to color monitor 15 via color lookup device 13. Data is not stored during this process, which is intended to allow the operator to check for proper functioning of the video system. The control program then interrogates for input of an escape character from the host computer (block 128). If an escape character is received the control program turns off (block 129) video ADC 10.

Function 130 ("Return to Main Menu?"): If this function is selected control program starts over again by returning to block 100.

Figure 12:
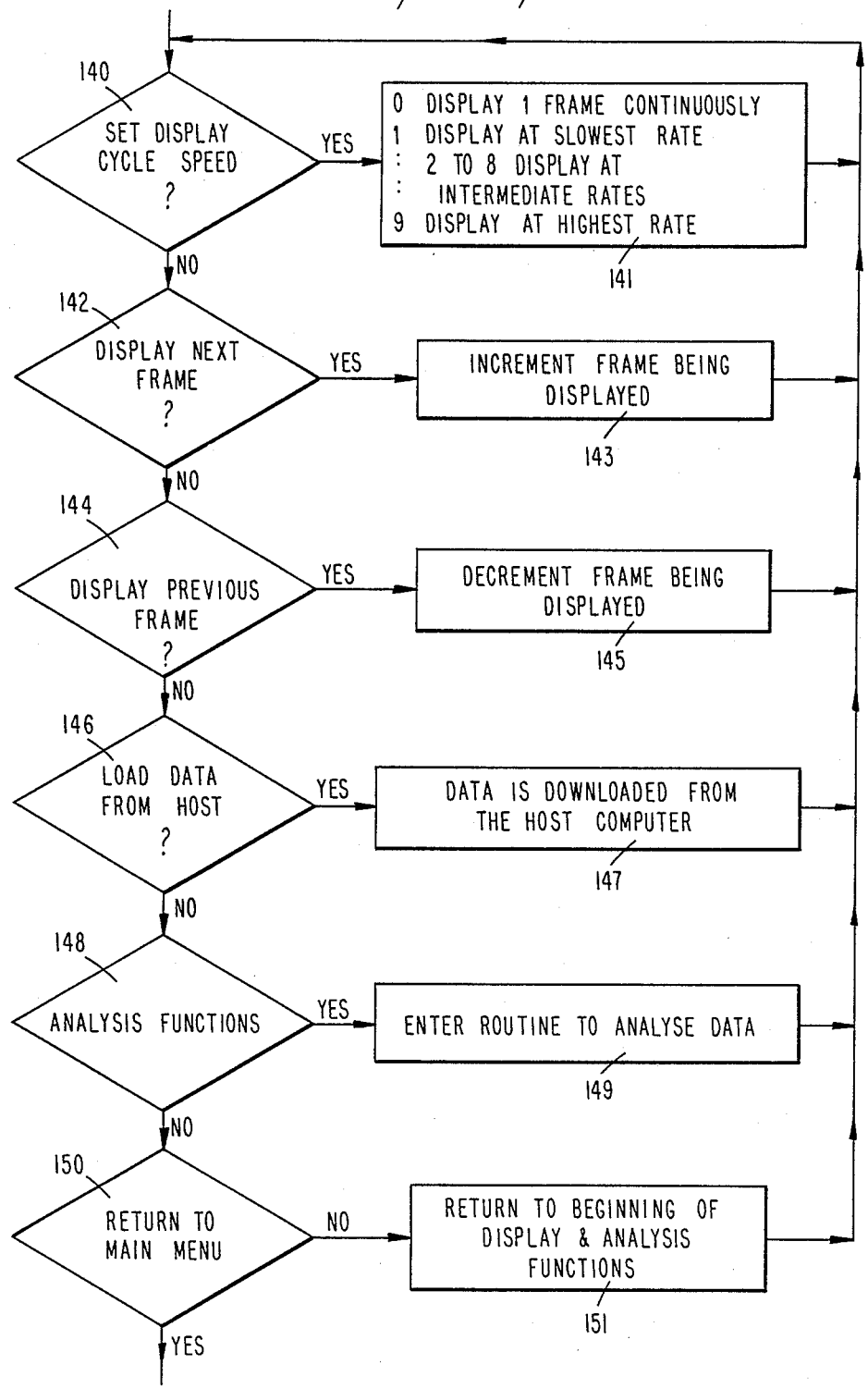
FIG. 12 is a flow chart of the display and analysis functions in the control program of the present invention.

Referring to FIG. 12, a flow chart for the display and analysis functions is shown. This part of the control program allows the operator to direct CPU 23 to carry out various functions as follows:

Function 140 ("Set Display Cycle Speed?"): This function controls the repetition rate for display of the sequential samples of pressure data. This function is selected (block 141) by inputting a number between 0 and 9 from the host computer. A value of 9 selects the highest possible rate for display. Progressively lower values will slow the rate down until a value of 0 which "freezes" the display at the currently displayed frame.

Function 142 ("Display Next Frame?"): This function is selected by inputting a space character from host computer 28. It causes the displayed frame to be incremented (block 143), allowing the operator to step through the display of sequential pressure data (in combination with selecting the frame display rate value 0).

Function 144 ("Display Previous Frame?"): This function is selected by inputting the minus character from host computer 28. It causes the displayed frame to be decremented (block 145), allowing the operator to step backwards through the display of sequential pressure data (in combination with selecting the frame display rate value 0).

Function 146 ("Load Data from Host?"): This function instructs host computer 28 to download (block 147) a file of previously collected pressure data to video RAM 16. This data is calibrated by host computer 28 before downloading. Once in video RAM 16, the data is displayed on color monitor 15 via color lookup table 13.

Function 148 ("Analysis Functions?"): When host computer requests this function the control program enters the flow chart shown in FIG. 13 at point 160. These functions are described below.

Function 150 ("Return to Main Menu?"): When host computer 28 requests this function the control program returns to the beginning (block 100) of the flow chart in FIG. 10. If this function is not requested, the control program stays in the "Display and Analysis Functions" and continues testing for requests.

Referring to FIG. 13, a flow chart illustrating the Analysis Functions is shown. This part of the control program allows the operator to interactively test areas of interest in the pressure data for further analysis, as described below:

Function 160 ("Set Area Size?"): This function allows the operator to set the size of the area of interest. This is done by incrementing or decrementing the radius of area (block 161). Host computer 28 sends data to video RAM 16 which produces an image of the circle of selected radius on color monitor 15.

Function 162 ("Move to New Area?"): If this function is selected, host computer 28 re-draws the circle for the area of interest in video RAM 16 at new co-ordinates. This allows the operator to reposition the area of interest on the screen.

Function 164 ("Enter Area?"): This function allows host computer 28 to re-draw the circle for the area of interest in a different color, and this circle is then retained on the image. The circles position and radius are saved (block 165) by host computer 28 for incorporation into the data file.

Function 166 ("Set New Top Point?"): When host computer 28 selects this function the pressure data in each frame of information is repositioned to coordinates provided by host computer 28 (block 167). This has the effect of repositioning the data on the color monitor display.

Function 168 ("Analyse?"): When host computer 28 selects this function CPU 23 generates data into video RAM 16 to draw graphs of maximum pressure against time (block 169) within each area of interest selected. The data for the graphs is obtained by searching each frame of video data in video RAM 16 for a value for maximum pressure within each of the indicated areas.

Function 170 ("Save Areas?"): When this function is selected host computer 28 saves the pressure data together with the information on circle position and radius for the selected areas of interest (block 17).

Function 172 ("Return to Display & Analysis Functions?"): When this function is requested by host computer 28 the control program returns to block 140 in FIG. 12. Otherwise the control program returns to the beginning of the Analysis functions, block 160.

As indicated by the foregoing description of the control program, the system permits the user to modify the displayed video data. For example, if he wants to draw a circle in a specified color around a particular area of interest in one video frame, the corresponding pixel elements are changed to a digital value corresponding to that color. This is done in a conventional manner using a separate "graphics" frame which has zero values for its pixels everywhere. The pixel values for the desired circle are added to the corresponding pixel "zeros" in the graphics frame to generate the desired color therein. The graphics frame is then displayed after the last frame containing pressure data. Since the system cycles through the frames at a sufficiently fast repetition rate (e.g., 30 frames per second), the circle generated by the graphics frame appears to be superimposed on the other frames.

Obviously, numerous additional modifications and variations of the present invention are possible in light of the above teachings. It is therefore to be understood that within the scope of the appended claims the invention may be practiced otherwise than as specifically described herein.

What is claimed as new and desired to be secured by letters patent of the United States is:

1. A foot pressure measurement system comprising:
   (a) a glass plate,
   (b) a reflective material comprising photographic paper positioned above said glass plate for receiving foot pressure,
   (c) a light source for generating light within said glass plate,
   (d) a mirror positioned below said glass plate for reflecting light emitted through said glass plate,
   (e) a television camera for receiving light reflected from said mirror, and
   (f) means for processing and displaying data indicative of said foot pressure.

2. The foot pressure measurement system of claim 1, wherein said reflective material comprises resin coated photographic paper and wherein said photographic paper is fixed and placed white side down on the upper surface of said glass plate.

3. The foot pressure measure measurement system of claim 1, further comprising:
   (g) means for converting force applied to the upper surface of said glass plate into electrical signals.

4. The foot pressure measurement system of claim 3, wherein said force converting means comprises a plurality of force transducers positioned in contact with the underside of said glass plate 5. A foot pressure measurement system comprising:
   (a) a glass plate,
   (b) a reflective material positioned above said glass plate for receiving foot pressure,
   (c) a light source for generating light within said glass plate,
   (d) a mirror positioned below said glass plate for reflecting light emitted through said glass plate,
   (e) a television camera for receiving light reflected from said mirror, and
   (f) means for processing and displaying data indicative of said foot pressure, including means for reducing background data generated in the absence of foot pressure on said reflective material.

6. The foot pressure measurement system of claim 5, wherein said background data reducing means comprises:
   (1) storage means for storing (a) digital data corresponding to a first video frame for which no foot pressure is applied to said glass and (b) digital data corresponding to a second video frame for which foot pressure is applied to said glass;
   (2) first subtraction means for subtracting the digital data for said first video frame from the digital data for said second video frame on a pixel-by-pixel basis;
   (3) second subtraction means for subtracting a constant value from each pixel value determined by said first subtraction means;
   (4) zero-setting means for setting to zero each pixel value of said second subtraction means if said pixel output value is negative; and
   (5) adding means for adding said constant value to each pixel value determined by said zero-setting means.

7. The foot pressure measurement system of claim 5, further comprising:
   (g) means for converting force applied to the upper surface of said glass plate into electrical signals indicative of said force.

8. The foot pressure measurement system of claim 7, wherein said force converting means comprises a plurality of force transducers positioned in contact with the underside of said glass plate.

9. A foot pressure measurement system comprising:
   (a) a glass plate
   (b) a reflective material comprising photographic paper positioned above said glass plate for receiving foot pressure,
   (c) a light source for generating light within said glass plate,
   (d) a mirror positioned below said glass plate for reflecting light emitted through said glass plate,
   (e) a television camera for receiving light reflected from said mirror and
   (f) means for processing and displaying data indicative of said foot pressure, including means for reducing background data generated in the absence of foot pressure on said reflective material.

10. The foot pressure measurement system of claim 9, wherein said background data reducing means comprises:

(1) storage means for storing (a) digital data corresponding to a first video frame for which no foot pressure is applied to said glass and (b) digital data corresponding to a second video frame for which foot pressure is applied to said glass;

(2) first subtraction means for subtracting the digital data for said first video frame from the digital data for said second video frame on a pixel-by-pixel basis;

(3) second subtraction means for subtracting a constant value from each pixel value determined by said first subtraction means;

(4) zero-setting means for setting to zero each pixel value of said second subtraction means if said pixel output value is negative; and (5) adding means for adding said constant value to each pixel value determined by said zero-setting means.

11. The foot pressure measurement system of claim 9, wherein said reflective material comprises resin coated photographic paper.

12. The foot pressure measurement system of claim 9, further comprising:

(g) means for converting force applied to the upper surface of said glass plate into electrical signals indicative of said force.

13. The foot pressure measurement system of claim 12, wherein said force converting means comprises a plurality of force transducers positioned in contact with the underside of said glass plate.

14. A method for measuring foot pressure comprising:

(a) detecting the intensity of light reflected from a support surface on which said foot pressure is applied;

(b) converting said reflected light into a first television signal wherein the intensity of each pixel of said television signal corresponds to the pressure applied at a particular location of said foot on said support surface;

(c) converting said television signal into digital data;

(d) substantially eliminating from said digital data any data corresponding to background signals generated in the absence of applied foot pressure;

(d) processing the resulting data into a second television signal suitable for display on a color video monitor; and (e) displaying said second television signal.

* * * * *